(12) United States Patent
Ramachandran et al.

(10) Patent No.: US 9,598,331 B2
(45) Date of Patent: Mar. 21, 2017

(54) OLEFIN CONVERSION PROCESS

(71) Applicant: Lummus Technology Inc., Bloomfield, NJ (US)

(72) Inventors: Bala Ramachandran, Easton, PA (US); Sukwon Choi, Clifton, NJ (US)

(73) Assignee: Lummus Technology Inc., Bloomfield, NJ (US)

( * ) Notice: Subject to any disclaimer, the term of this patent is extended or adjusted under 35 U.S.C. 154(b) by 210 days.

(21) Appl. No.: 14/548,509

(22) Filed: Nov. 20, 2014

(65) Prior Publication Data

US 2015/0141722 A1 May 21, 2015

Related U.S. Application Data

(60) Provisional application No. 61/906,647, filed on Nov. 20, 2013.

(51) Int. Cl.
*C07C 6/04* (2006.01)
*C07C 6/02* (2006.01)
(Continued)

(52) U.S. Cl.
CPC ............... *C07C 6/04* (2013.01); *B01J 8/0453* (2013.01); *C07C 5/2512* (2013.01); *B01J 2208/025* (2013.01); *B01J 2219/00006* (2013.01)

(58) Field of Classification Search
None
See application file for complete search history.

(56) References Cited

U.S. PATENT DOCUMENTS 5,162,597 A * 11/1992 Wu ..................... B01J 23/30
585/646
6,884,917 B1 * 4/2005 Coleman ................. C07C 6/04
585/643
(Continued)

FOREIGN PATENT DOCUMENTS

WO 2009-145834 A1 12/2009

OTHER PUBLICATIONS

International Search Report and Written Opinion issued Mar. 10, 2015 in corresponding International Application No. PCT/US2014/0966420 (10 pages).

*Primary Examiner* — In Suk Bullock
*Assistant Examiner* — Philip Louie
(74) *Attorney, Agent, or Firm* — Osha Liang LLP

(57) ABSTRACT

Processes for the production of high purity alpha olefins from a mixture of olefins are disclosed. The processes may include: contacting propylene and a hydrocarbon mixture comprising a mixture of olefins having a carbon number n with a first metathesis catalyst to form a metathesis product comprising a beta-olefin having a carbon number n+1, an alpha-olefin having a carbon number n−1, as well as any unreacted propylene and olefins having a carbon number n. The metathesis product may be fractionated to recover a fraction comprising the beta-olefin having a carbon number n+1. Ethylene and the fraction comprising the beta-olefin having a carbon number n+1 may then be contacted with a second metathesis catalyst to form a second metathesis product comprising an alpha-olefin having a carbon number n and propylene, which may be fractionated to form a propylene fraction and a fraction comprising the alpha olefin having a carbon number n.

22 Claims, 6 Drawing Sheets

(51) Int. Cl.
*C07C 5/25* (2006.01)
*B01J 8/04* (2006.01)

(56) References Cited

U.S. PATENT DOCUMENTS

2002/0197190 A1 12/2002 Schwab et al.
2010/0145086 A1 6/2010 Schrodi et al.
2012/0245400 A1 9/2012 Clark et al.

* cited by examiner

OLEFIN CONVERSION PROCESS

BACKGROUND OF DISCLOSURE

Field of the Disclosure

Embodiments disclosed herein relate generally to the production of high purity alpha-olefins, such as $C_4$ to $C_8$ olefins, for use in various downstream processes, such as use as a co-monomer in the production of polyethylenes and polypropylenes, among other end uses. More specifically, embodiments disclosed herein relate to the more efficient production and purification of alpha-olefins utilizing isomerization and metathesis.

Background

Processes for producing high purity polymer-grade comonomers include various 1-butene comonomer production processes and 1-hexene comonomer production processes. These processes utilize metathesis and/or double-bond isomerization reactions that occur over specific catalysts using mixed n-butenes as the feed to produce polymer-grade 1-butene and 1-hexene used as comonomers for production of polyethylene. However, these processes are extremely energy intensive as they employ distillation to separate the desired alpha-olefin (1-butene and 1-hexene) with high purity from mixtures of their positional isomers that exhibit very close boiling points (2-butene and 2-hexene, 3-hexene, respectively).

For example, the 1-butene process flow includes a butenes superfractionator that separates the 1-butene product from 2-butene. The 1-hexene process is even more energy intensive as it requires two superfractionators: a butenes superfractionator to separate a high-purity 1-butene stream used to produce hexenes, and a hexenes superfractionator to separate the final 1-hexene product from the other positional hexene isomers (2-hexene and 3-hexene).

The high operating costs associated with the energy intensive distillation towers in the processes render them economically less attractive, especially for the 1-hexene process that requires two (2) superfractionators. Similar processes for production of 1-octene would be even more separation intensive, separating 1-octene from a mixture of 2-, 3-, and 4-octene.

SUMMARY OF THE DISCLOSURE

In one aspect, embodiments disclosed herein relate to a process for the production of olefins. The process may include: contacting propylene and a hydrocarbon mixture comprising a mixture of olefins having a carbon number n with a first metathesis catalyst to form a metathesis product comprising a beta-olefin having a carbon number n+1, an alpha-olefin having a carbon number n−1, as well as any unreacted propylene and olefins having a carbon number n; fractionating the metathesis product to recover a fraction comprising the beta-olefin having a carbon number n+1; contacting ethylene and the fraction comprising the beta-olefin having a carbon number n+1 with a second metathesis catalyst to form a second metathesis product comprising an alpha-olefin having a carbon number n and propylene; fractionating the second metathesis product to form a propylene fraction and a fraction comprising the alpha olefin having a carbon number n.

In another aspect, embodiments disclosed herein relate to a process for producing high purity 1-butene. The process may include: contacting a hydrocarbon mixture comprising linear butenes with an isomerization catalyst to form an isomerization product comprising 2-butenes and 1-butenes; contacting propylene and the isomerization product with a first metathesis catalyst to form a first metathesis product comprising 2-pentene, propylene, unreacted $C_4$ olefins, ethylene, and 3-hexene; fractionating the first metathesis product to recover an ethylene fraction, a propylene fraction, a butene fraction, and a 2-pentene fraction; contacting the 2-pentene fraction and ethylene with a second metathesis catalyst, which may be the same or different than the first metathesis catalyst, to form a metathesis effluent comprising ethylene, propylene, 1-butene, and any unreacted 2-pentene; fractionating the metathesis effluent to recover a 1-butene fraction, a C3− fraction, and a C5+ fraction.

In another aspect, embodiments disclosed herein relate to a process for producing high purity 1-hexene. The process may include: isomerizing and metathesizing a mixed C4 olefin stream comprising 1-butene and 2-butene to produce a first reaction product comprising ethylene, propylene, unreacted butenes, 2-pentene, and 3-hexene; isomerizing and metathesizing a mixed C5 olefin stream comprising 1-pentene and 2-pentene to produce a second reaction product comprising ethylene, propylene, n-butenes, unreacted pentenes, 3-hexene, 3-heptene, 2-hexene, and 4-octene; isomerizing and metathesizing propylene and a mixed C6 olefin stream comprising 1-hexene, 2-hexene, and 3-hexene to produce a third reaction product comprising ethylene, n-butenes, n-pentenes, and 2-heptene; fractionating the first, second, and third reaction products to recover an ethylene fraction, a propylene fraction, a butene fraction, a pentene fraction, a hexene fraction, and a heptene fraction comprising 2-heptene; metathesizing ethylene and the 2-heptene in the heptene fraction to form a metathesis product comprising propylene, 1-hexene, and any unreacted ethylene and 2-heptene; fractionating the metathesis product to recover an C5− fraction, a 1-hexene product fraction, and a C7+ fraction.

In another aspect, embodiments disclosed herein relate to a process for producing high purity 1-octene. The process may include: isomerizing and metathesizing a mixed C4 olefin stream comprising 1-butene and 2-butene to produce a first reaction product comprising ethylene, propylene, unreacted butenes, 2-pentene, and 3-hexene; isomerizing and metathesizing a mixed C5 olefin stream comprising 1-pentene and 2-pentene to produce a second reaction product comprising ethylene, propylene, n-butenes, unreacted pentenes, 3-hexene, 3-heptene, 2-hexene, and 4-octene; isomerizing and metathesizing propylene and a mixed C6 olefin stream comprising 1-hexene, 2-hexene, and 3-hexene to produce a third reaction product comprising ethylene, n-butenes, n-pentenes, and 2-heptene; isomerizing and metathesizing propylene and a mixed C7 olefin stream comprising 1-heptene, 2-heptene, and 3-heptene to produce a fourth reaction product comprising ethylene, n-butenes, n-pentenes, n-hexenes, and 2-octene; isomerizing and metathesizing propylene and a mixed C8 olefin stream comprising 1-octene, 2-octene, 3-octene, and 4-octene to produce a fifth reaction product comprising ethylene, n-butenes, n-pentenes, n-hexenes, and 2-nonene; fractionating the first, second, third, fourth, and fifth reaction products to recover an ethylene fraction, a propylene fraction, a butene fraction, a pentene fraction, a hexene fraction, a heptene fraction, an octene fraction, and a nonene fraction comprising 2-nonene; metathesizing ethylene and the 2-nonene in the nonene fraction to form a metathesis product comprising propylene, 1-octene, and any unreacted ethylene and 2-nonene; fractionating the metathesis product to recover an C7− fraction, a 1-octene product fraction, and a C9+ fraction.

DETAILED DESCRIPTION

Figure 1:
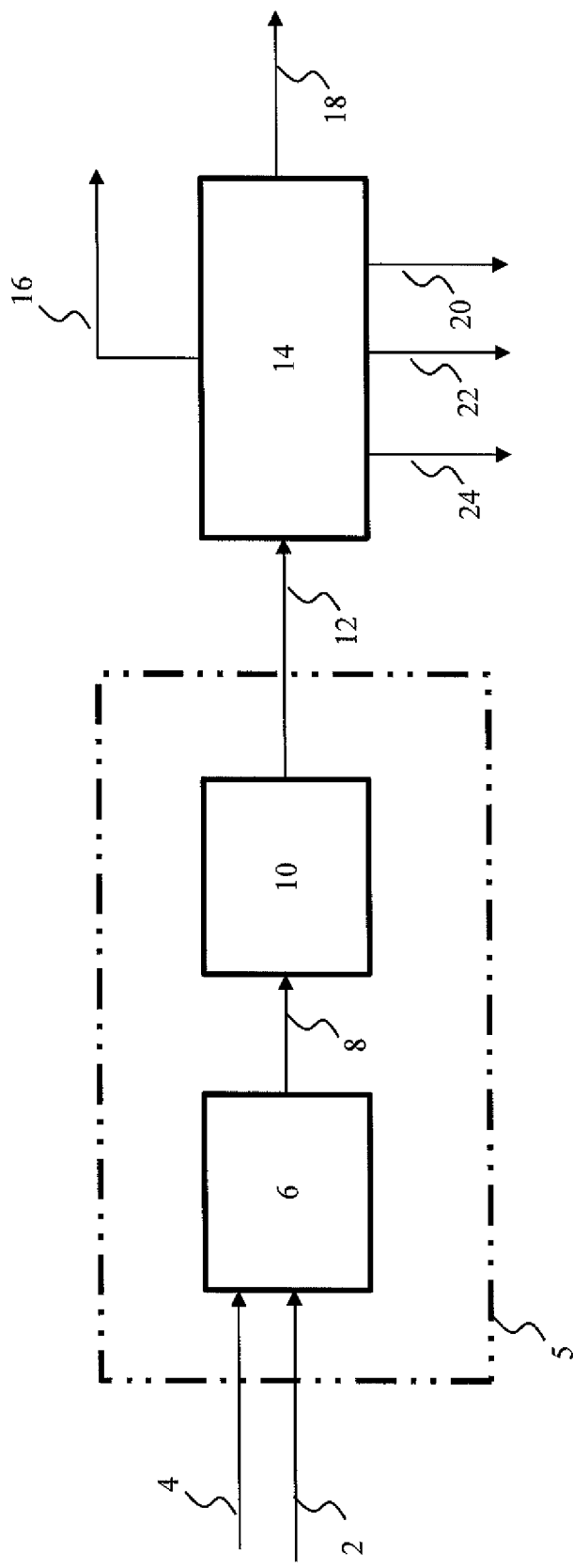
FIG. 1 is a simplified process flow diagram of a process for producing high purity 2-olefins according to embodiments disclosed herein.

In one aspect, embodiments herein relate to the production of high purity alpha olefins, such as 1-butene, 1-hexene, and 1-octene, from mixtures including their positional isomers. More specifically, embodiments disclosed herein relate to the more efficient production and purification of alpha-olefins utilizing isomerization and metathesis, where separations of the products may be performed with reduced need for or even without the need for intensive fractionation systems. In another aspect, embodiments disclosed herein relate to the production of an alpha olefin having a carbon number n via metathesis, first producing an intermediate beta olefin having a carbon number n+1, and then by converting the intermediate back to the alpha-olefin having a carbon number n.

Processes disclosed herein utilize isomerization to favor the production of a high purity beta-olefin, which is easily separable based on carbon number, and that may be used as a chemical intermediate for the production of a desired high purity alpha-olefin. Embodiments disclosed herein thus eliminate the need for the superfractionators commonly used for 1-butene and 1-hexene processes, as noted in the Background above. Similar improvements may result when producing other alpha-olefins from mixtures with their positional isomers.

Embodiments herein provide for systems and processes for the production of olefins, including alpha-olefins in the range from C4 to C8 or above. The process may include a first step of contacting propylene and a hydrocarbon mixture comprising a mixture of olefins having a carbon number n with a first metathesis catalyst to form a metathesis product comprising a beta-olefin having a carbon number n+1, an alpha-olefin having a carbon number n−1, as well as any unreacted propylene and olefins having a carbon number n. The metathesis product may then be fractionated to separate the beta-olefin having a carbon number n+1 from the lighter hydrocarbons.

Ethylene and the fraction comprising the beta-olefin having a carbon number n+1 may then be contacted with a second metathesis catalyst to form a second metathesis product comprising an alpha-olefin having a carbon number n and propylene. The second metathesis product may then be fractionated to recover a propylene fraction and a fraction comprising the alpha olefin having a carbon number n.

In some embodiments, the process may be used to form high purity 1-butene, 1-pentene, 1-hexene, 1-heptene, 1-octene as well as high purity alpha-olefins of greater carbon numbers. Feed streams that may be used to form such high purity alpha olefins may include olefins and olefin mixtures, which may be mixed with alkanes, where the olefins in the feed may include $C_4$ to $C_n$ olefins, where the $C_n$ alpha olefin is desired.

The main reaction of the processes disclosed herein is the formation of a beta-olefin (n+1) from the reaction of propylene with a mixture of olefins of the same carbon length (n). However, the internal olefins of carbon number n react with propylene by metathesis to create olefins that are shorter in length compared to the feed olefin (n−x, where x is 1, 2, etc.).

The metathesis reaction with propylene creates a product stream containing unreacted feed olefins mixtures with carbon length n, products with a lower carbon length than n, and a beta-olefin of carbon length n+1. As a result, the easier separation of the beta-olefin of carbon length n+1 from all the other hydrocarbons may be achieved.

For example, as illustrated in FIG. 1, propylene stream 4 and a feed stream 2 including a mixture of positional isomers of carbon number n may be fed to an isomerization/metathesis reaction zone 5. The isomerization/metathesis reaction zone 5 may include an upstream reaction zone 6 to perform double-bond isomerization of the olefin mixture (such as n-hexenes) to form an equilibrium mixture 8 of the positional isomers (such as 1-hexene, 2-hexene, and 3-hexene), followed by a downstream reaction zone 10 to perform metathesis of the alpha olefin isomer with propylene from the reaction zone 6. The isomerization zone may be operated at conditions favoring the production of the 1-isomer. This segregated reaction zone configuration allows for the use of any mixture of n-olefins as feed 2 to exclusively produce a constant high-purity 2-olefin of carbon number n+1 (i.e., without the positional 1-olefin isomer having carbon number n+1) and ethylene product stream 12 at high product selectivities (>90%) and with little by-products. Separation of the 2-olefin of carbon number n+1 may then be performed in a fractionation system 14 to separate the ethylene 16, unreacted propylene 18, unreacted n-olefin of carbon number n 20, and the target 2-olefin of carbon number n+1 (fraction 22).

The pure stream of the beta-olefin of carbon length n+1 may then be reacted with ethylene by metathesis to obtain a pure stream of the original alpha-olefin with carbon length n and propylene as a by-product, along with unreacted beta-olefin of carbon length n+1 and ethylene. Separation of the alpha-olefin with carbon length n is now significantly easier as no other positional isomer (internal olefin isomers of the alpha-olefin of carbon length n is present in the reactor product mixture).

Thus, processes according to embodiments herein may eliminate the need for the energy intensive separation by distillation of the alpha-olefin from its positional isomers. Additionally, as can be readily seen, the process may be used to separate and purify any alpha-olefin from its positional isomers.

High Purity 1-Butene Production

As briefly described above, high purity 1-butene may be achieved by isomerization and metathesis. The first reaction zone may be used to achieve a high relative ratio of 1-butene to 2-butene via isomerization and to produce a high purity 2-pentene product from the mixture of n-butenes. The 2-pentene may then be converted by metathesis back into a 1-butene recoverable at high purity through relatively easy distillation processes (i.e., no superfractionators required).

The isomerization and metathesis in the first reaction zone may be performed in segregated reaction zones, in the same or different reactors, thus limiting the isomerization and cross-metathesis of the desired 2-pentene intermediate. For example, when contained in the same reactor, such as a downflow reactor, the segregated reactions may be performed with a catalyst bed configuration including an upper section to perform double-bond isomerization of n-butenes (1-butene and 2-butene) and a lower section to perform cross-metathesis between the formed 1-butene and 2-butene. This catalyst bed configuration allows for the use of any mixture of n-butenes as feed to exclusively produce a high-purity 2-pentene (with essentially no 1-pentene) and propylene stream at high equilibrium product selectivities (>90%) with low levels of ethylene and hexene formation.

The formed 2-pentene stream can then be easily separated from co-product propylene without the use of an intensive separation scheme, e.g., superfractionation. This high-purity 2-pentene stream attained may then be further processed to produce high purity 1-butene via metathesis of the 2-pentene with ethylene.

Embodiments disclosed herein circumvent the need to separate the 1-butene from its positional isomer (2-butene) by distillation in a superfractionator. This is a major improvement for the current comonomer production processes, as it eliminates a highly energy intensive butenes superfractionator from 1-butene production processes. This makes the processes to make 1-butene and 1-hexene economically more attractive.

Figure 2:
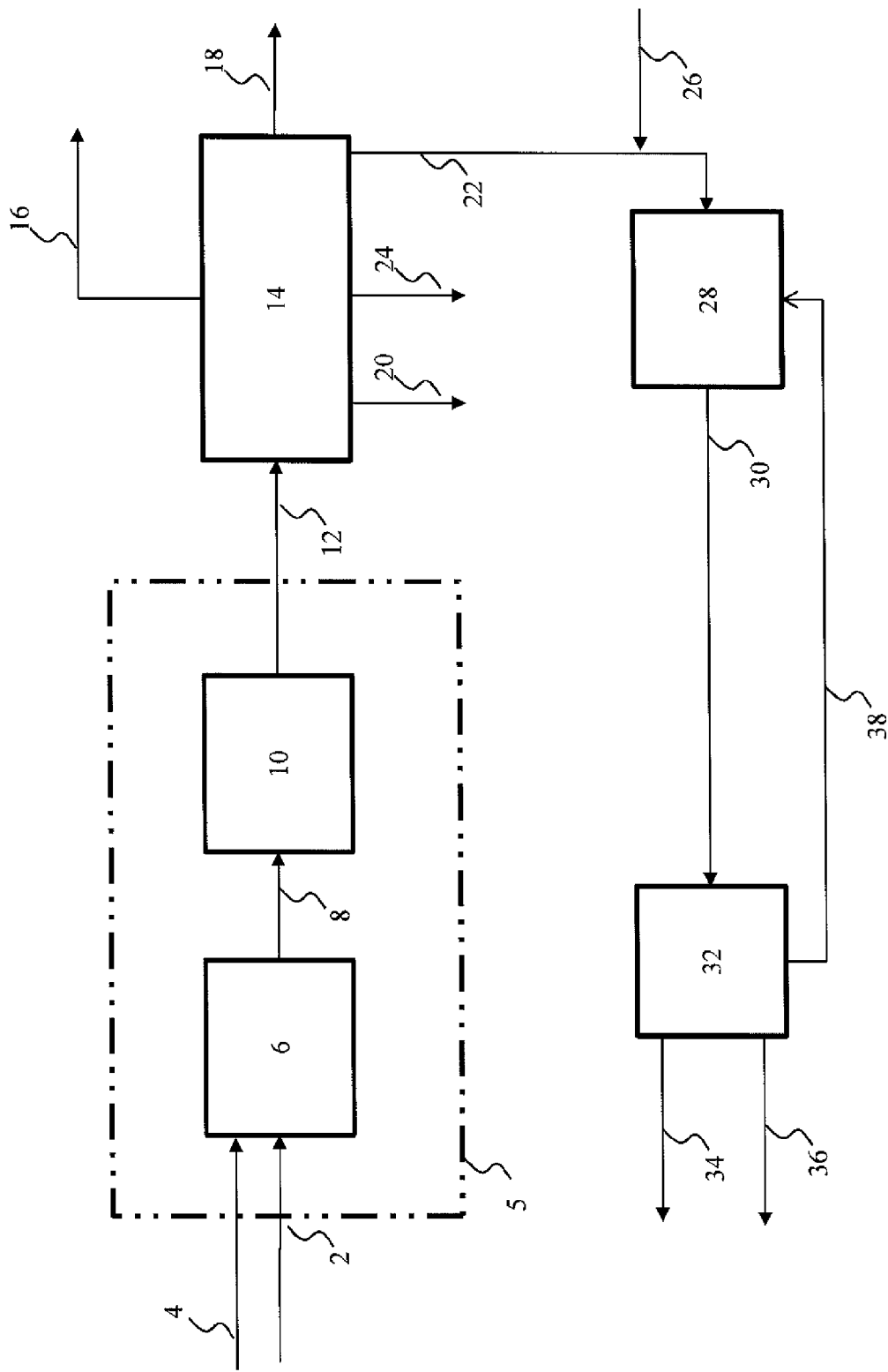
FIG. 2 is a simplified process flow diagram of a process for producing high purity 1-butenes according to embodiments disclosed herein.

Referring now to FIG. 2, a simplified process flow diagram of a process for producing high purity alpha-olefins according to embodiments herein is illustrated. While described with respect to 1-butene, the process may be used for other alpha-olefin mixtures as described above.

A butenes feed stream 2, including a mixture of n-butenes (1-butene and 2-butene) at any ratio, may be fed along with propylene feed stream 4 to an isomerization/metathesis reaction zone 5, referred to herein as a segregated olefin conversion unit. In some embodiments, the segregated OCU (olefin conversion unit) is a reactor system 5 including one or more upstream reaction zones 6 to perform double-bond isomerization of n-butenes to form an equilibrium mixture 8 of 1-butene and 2-butenes, followed by one or more downstream reaction zone 10 to perform metathesis of 1-butene with propylene and cross-metathesis between the formed 1-butene and 2-butene products from the reaction zone 6. In each zone 6 and 8, the one or more reaction zones may be in parallel or series. This segregated reaction zone configuration allows for the use of any mixture of n-butenes as feed 2 to exclusively produce a constant high-purity 2-pentene (i.e., without 1-pentene) and ethylene product stream 12 at high product selectivities (>90%) and with little by-products, i.e., hexene. The formed 2-pentene stream 12 can be easily separated from the product mixture without the use of an intensive separation scheme, e.g., superfractionation, such as in a fractionation system 14, which may include a deethylenizer, a depropylenizer, and a debutenizer, separating the ethylene 16, propylene 18 and butenes 20 from the target 2-pentene product 22. If desired, a C6+ purge stream 24 may also be recovered.

Figure 3:
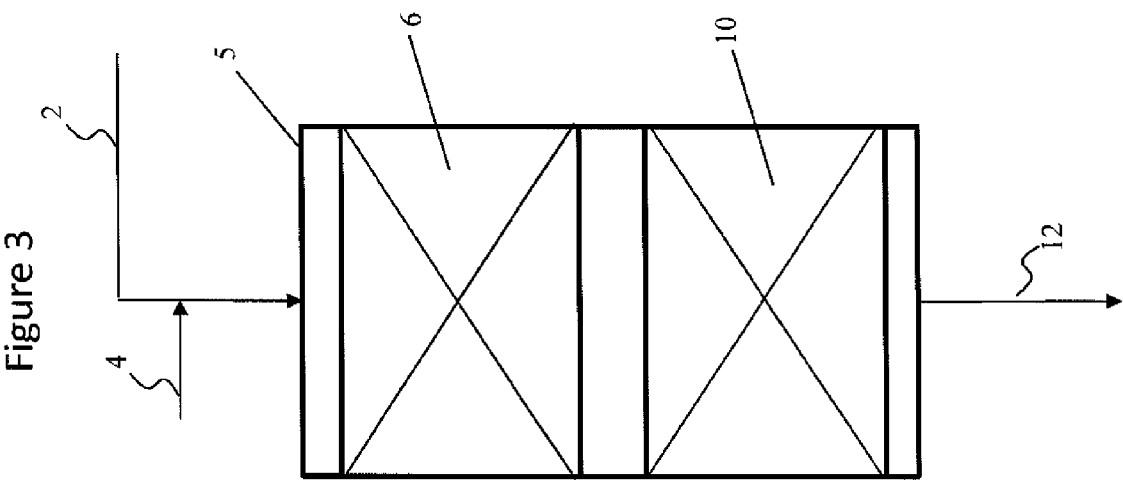
FIG. 3 is a simplified process flow diagram of an isomerization/metathesis reactor for use in processes for producing 1-olefins according to embodiments disclosed herein.

In some embodiments, the segregated OCU (olefin conversion unit) is a single downflow reactor 5, such as illustrated in FIG. 3, where like numerals represent like parts. Reactor 5 may include a catalyst bed 6 in the upper portion of the reactor 5 to perform double-bond isomerization of n-butenes to form an equilibrium mixture of 1-butene and 2-butenes, followed by a catalyst bed 10 in the lower portion of the reactor 5 to perform metathesis of propylene with 1-butenes and cross-metathesis between the formed 1-butene and 2-butene products from the upper reaction zone 6. This catalyst bed configuration allows for the use of any mixture of n-butenes as feed 2 to exclusively produce a constant high-purity 2-pentene (without 1-pentene) and propylene product stream 12 at high product selectivities (>90%) with little by-products, i.e., ethylene and hexene. The formed 2-pentene stream can be easily separated from the product mixture without the use of an extensive separation scheme, e.g., superfractionation, such as in a fractionation system 14 as described above.

Referring back to FIG. 2, the 2-pentene stream 22 may then be fed along with ethylene stream 26 to a metathesis reaction zone 28. Metathesis reaction zone 28 may include a metathesis catalyst that is the same or different than that contained in metathesis reaction zone 10. In metathesis reaction zone 28, the 2-pentene and ethylene may be contacted with a metathesis catalyst under suitable reaction conditions to convert the 2-pentene and ethylene into propylene and 1-butene. The effluent 30 from metathesis reaction zone 28 may thus include ethylene, propylene, 1-butene, and 2-pentene. Effluent 30 may then be fed to a fractionation system 32 for separation of the ethylene and propylene 34 from the 1-butene product 36 and the unreacted 2-pentene 38, which may be recycled back to reaction zone 28 for continued conversion.

In the 1-butene process, 1-butene in the n-butenes reacts with propylene in the segregated olefin conversion unit (isomerization/metathesis reaction zone 5) to make 2-pentene and ethylene. However, the 2-butene does not react with propylene (non-productive reaction where products equal reactants) and thus goes essentially unconverted in this reactor. The primary reactions taking place in this reactor are as follows.

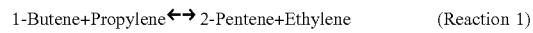

$$\text{1-Butene} + \text{Propylene} \leftrightarrow \text{2-Pentene} + \text{Ethylene} \quad \text{(Reaction 1)}$$

In the metathesis-only reactor (metathesis reaction zone 28), the 2-pentenes are reacted with ethylene to form propylene and 1-butene, the target product. The primary reactions taking place in this reactor are as follows.

$$\text{2-Pentene} + \text{Ethylene} \leftrightarrow \text{1-butene} + \text{Propylene} \quad \text{(Reaction 2)}$$

Figure 4:
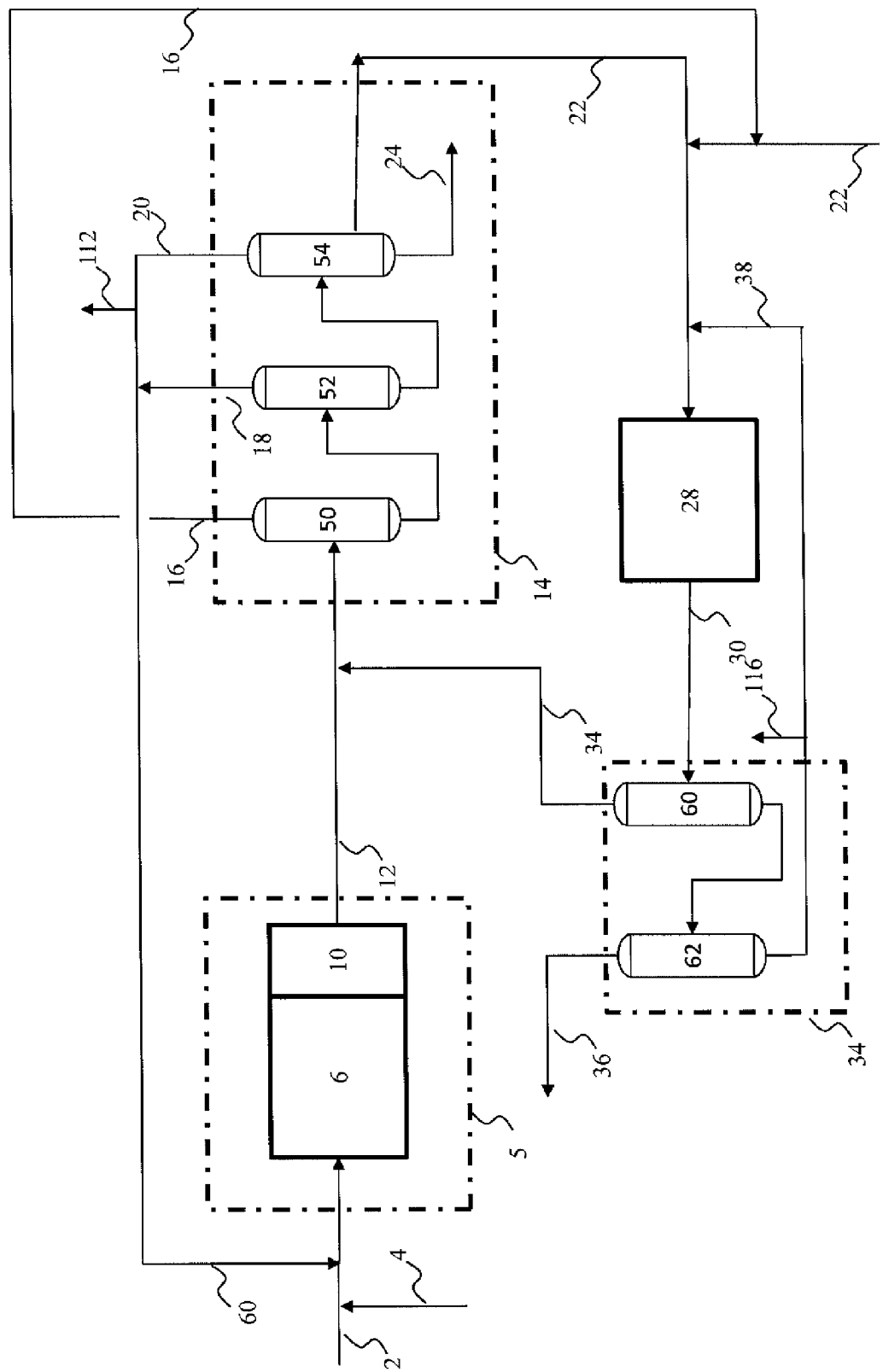
FIG. 4 is a simplified process flow diagram of a process for producing high purity 1-butenes according to embodiments disclosed herein.

As reactants and products of the two metathesis reaction zones 10, 28 are common, efficiencies may be realized by utilizing common fractionators and product recycle. One embodiment for the overall process to produce high purity 1-butene may be as illustrated in FIG. 4, where like numerals represent like parts. As described above, feed butenes 2, which may be a mixture of normal butenes, pure 1-butene, or pure 2-butene, and propylene 4 may be fed to reaction zone 5, including an isomerization zone 6 and a segregated metathesis zone 10, for producing an isomerization/metathesis product 12, including 2-pentene and ethylene.

The isomerization/metathesis product 12 may then be fed to a fractionation system 14 for separation of the products, byproducts, and unreacted reactants (normal butenes). Fractionation system 14 may include a deethylenizer 50, a depropylenizer 52, and a debutenizer 54. The deethylenizer 50 may be used to separate an ethylene fraction 16 from heavier hydrocarbons. The depropylenizer 52 may be used to recover a propylene fraction 18. The debutenizer 54 may be used to separate a C4 fraction 20 from a side draw fraction 22, including 2-pentenes, and a bottoms heavy fraction 24 (purge C6's). It is noted that the number of towers in the fractionation zones of embodiments herein may be reduced by employing distillation columns with side draws, if desired.

Propylene fraction 18 and/or butene fraction 20 may be recycled to the isomerization/metathesis reaction zone 5. Ethylene fraction 16 may be fed along with fresh ethylene 26, as needed, and 2-pentene fraction 22 to metathesis reaction zone 28 for conversion of the reactants to 1-butene and propylene.

The effluent 30 from metathesis reaction zone 28 may then be fed to a fractionation zone 34, which may include a depropylenizer 60 and a debutenizer 62. The entirety of fractionation zone 34 cannot be integrated with fractionation zone 14 as admixture of the desired 1-butene product with unreacted butenes in stream 12 would be counterproductive to achieving high purity 1-butene without use of a superfractionator.

Depropylenizer 60 may be used to separate ethylene and propylene from effluent 30. The ethylene and propylene fraction 34 may then be combined with effluent 12 for separation of the ethylene and propylene in fractionators 50, 52 of fractionation system 14. Debutenizer 62 may be used to separate the 1-butene product fraction 36 from any unreacted 2-pentenes 38, which may be recycled to reaction zone 28 for continued conversion.

Overall, the system may be essentially neutral with respect to propylene and ethylene usage. Propylene is used to convert the butenes mixture to 2-pentene and ethylene, and ethylene is used to convert the 2-pentene back to 1-butene and propylene. Thus, recovery and recycle of ethylene and propylene within the system may result in a low net usage of both raw materials.

Similar processes may be used to produce a high purity alpha-olefin from a mixture of positional isomers, including C5, C6, C7, and C8 olefin mixtures. Flow schemes similar to that of FIG. 4 may be used to produce, for example, a high purity 1-hexene stream from a mixture of n-hexenes, reaction zone 5 producing 2-heptene from a mixture of n-hexenes and propylene, and reaction zone 28 producing pure 1-hexene via reaction of the 2-heptene with ethylene.

Additionally, embodiments disclosed herein may also be used to improve the production of 1-hexene and 1-octene from a mixture of n-butenes. Portions of the flow schemes may take advantage of the n to n+1 via propylene metathesis and the n+1 to alpha-olefin of carbon number n via ethylene metathesis. Two possible flow schemes are described below, where the flow schemes provide additional reactors to maximize the target olefin production via isomerization and metathesis of other reaction feeds and byproducts.

Production of High Purity 1-Hexene from N-Butenes

Figure 5:
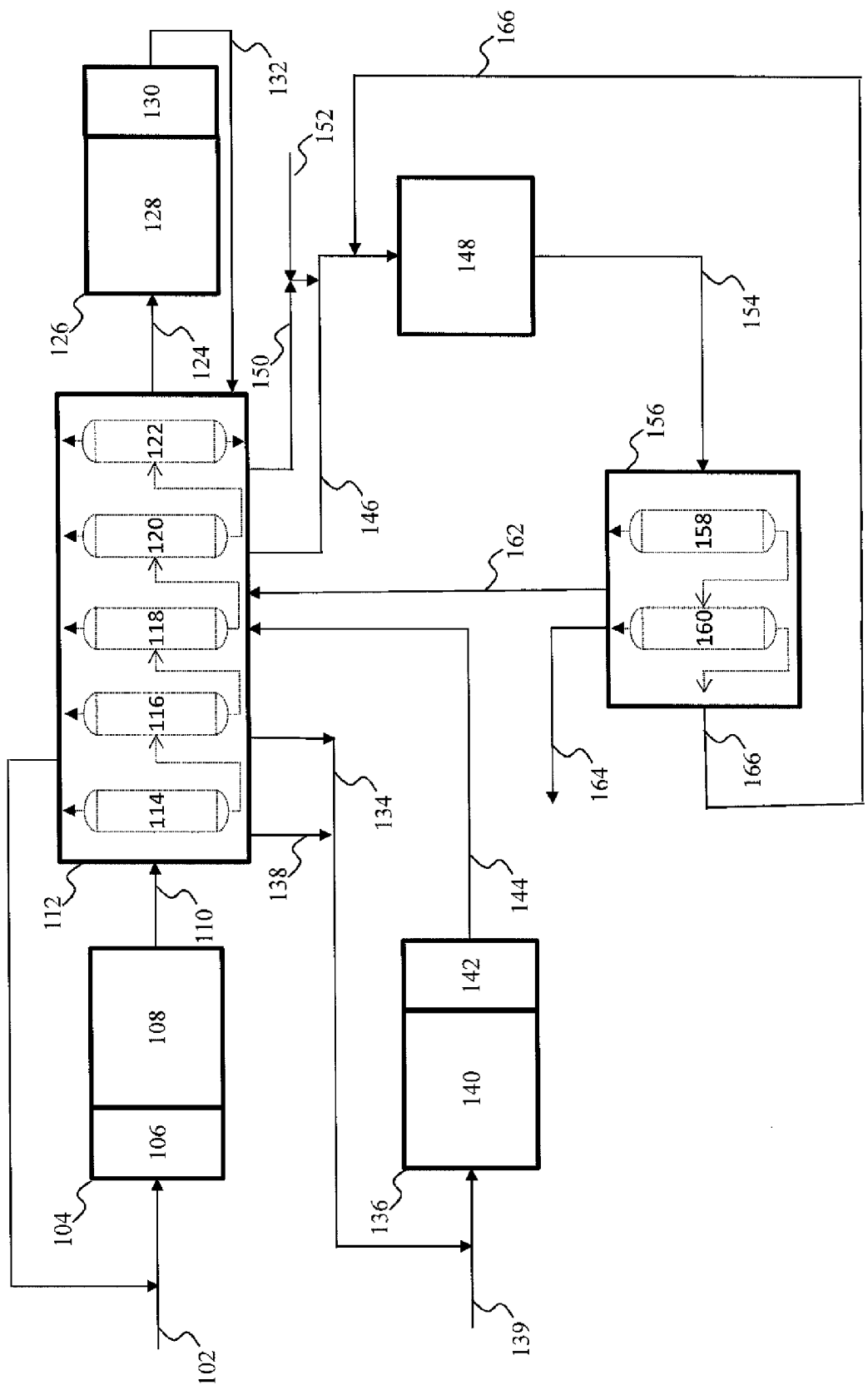
FIG. 5 is a simplified process flow diagram of a process for producing high purity 1-hexenes according to embodiments disclosed herein.

FIG. 5 is a simplified process flow diagram of a process for the production of 1-hexene from a mixture of n-butenes according to embodiments herein. A mixed n-butenes stream 102 is fed into an olefin conversion unit 104, which may include an upstream bed 106 of isomerization catalyst, such as MgO, and a downstream mixed catalyst bed 108 including a mixture of isomerization catalyst and metathesis catalyst, such as a 3:1 mixture of isomerization to metathesis catalyst. The n-butenes may be derived, for example, from the bottoms of a catalytic distillation unit (not shown) for separating linear butenes from isobutenes. The olefin conversion unit 104 converts 1-butene and 2-butene by isomerization and metathesis to ethylene, propylene, 2-pentene, and 3-hexene.

The reactor effluent 110 is then fed to the main separation train 112 for separation of the various products. The separation train 112 may include, for example, a deethylenizer 114, a depropylenizer 116, a debutanizer 118, a depentenizer 120, and a dehexenizer 122, among other possible configurations. For convenience, the flow streams are illustrated to/from the train 112, as opposed to the individual distillation towers.

The pentenes from the overhead 124 of the depentenizer are fed to a segregated olefin conversion unit 126. The segregated olefin conversion unit 126 may include an upstream bed 128 of isomerization catalyst and a downstream bed 130 of metathesis catalyst similar to that as described above. In the segregated OCU 126, 1-pentene and 2-pentene are isomerized in the isomerization reaction zone, producing an equilibrium mixture of 1-pentene and 2-pentene, which then react in the metathesis reaction zone to produce ethylene, propylene, butenes, 2-hexene, 3-hexene, 2-heptene, and 4-octene. The effluent 132 from the segregated OCU 126 are also fed to the main separation train 112.

The hexenes from the overhead 134 of the dehexenizer are fed to a segregated OCU 136 along with propylene 138 from the overhead of the depropylenizer and any fresh propylene 139, as needed. The segregated OCU 136 may include an upstream bed 140 of isomerization catalyst and a downstream bed 142 of metathesis catalyst as described above. A molar ratio of propylene to hexenes may be maintained in the range of 1:1 to 10:1. In the isomerization reaction zone 140, an equilibrium mixture of 1-hexene, 2-hexene, and 3-hexene is produced. The 1-hexene then reacts with propylene in the metathesis reaction zone 142 to form ethylene and 2-heptene. The other hexenes react with propylene and ethylene to form butenes and pentenes. The effluent 144 from the segregated OCU 136 are also fed to the main separation train 112.

The bottoms 146 from the dehexenizer, including 2-heptene, are fed to a metathesis reaction zone 148 along with ethylene 150 from the overhead of the deethylenizer and any fresh ethylene 152, as needed. The feed to the metathesis reaction zone may be controlled to have a molar ratio of ethylene to (heptenes+octenes) in the range from about 1:1 to about 15:1. 2-Heptene reacts with ethylene to form the 1-hexene product and propylene. 3-Heptene reacts with ethylene to form 1-butene and 1-pentene. 4-octene reacts with ethylene to yield two moles of 1-pentene. The reactor effluent 154 is then sent to a second separation train 156 including a depentenizer 158 and a dehexenizer 160. The overhead 162 from the depentenizer is fed back to the front of the main separation train 112. 1-Hexene product 164 is collected from the overhead of the dehexenizer. The bottoms 166 of the dehexenizer contain unreacted heptenes and octenes, and may be recycled back to the metathesis reactor 148 for continued conversion.

The reactions taking place in the various reactors are listed below.

Olefin Conversion Unit 104:
1-Butene+2-Butene↔Propylene+2-Pentene
1-Butene+1-Butene↔ethylene+3-hexene
Segregated OCU 126
2-pentene+2-pentene↔2-butene+3-hexene
1-pentene+2-pentene↔propylene+3-heptene
2-pentene+2-pentene↔1-butene+2-hexene
1-pentene+1-pentene↔1-butene+2-pentene
Segregated OCU 136
1-hexene+propylene↔2-heptene+ethylene
2-hexene+propylene↔2-butene+1-pentene
3-hexene+propylene↔1-butene+2-pentene
Metathesis Reactor 148
2-heptene+ethylene↔1-hexene+propylene 3-heptene+ethylene↔1-butene+1-pentene
4-octene+ethylene↔1-pentene+1-pentene.

Depending on the amount of isobutene in the fresh n-butenes feed, purges (not illustrated) may be taken in each of the C4, C5, C6, and C7 recycle streams, such as to prevent isobutene, isopentene, and isohexene buildup. If alkanes are present in the mixed hydrocarbon feed, purge streams may also be provided to avoid buildup of the alkanes.

Production of 1-Octene from N-Butenes

Figure 6:
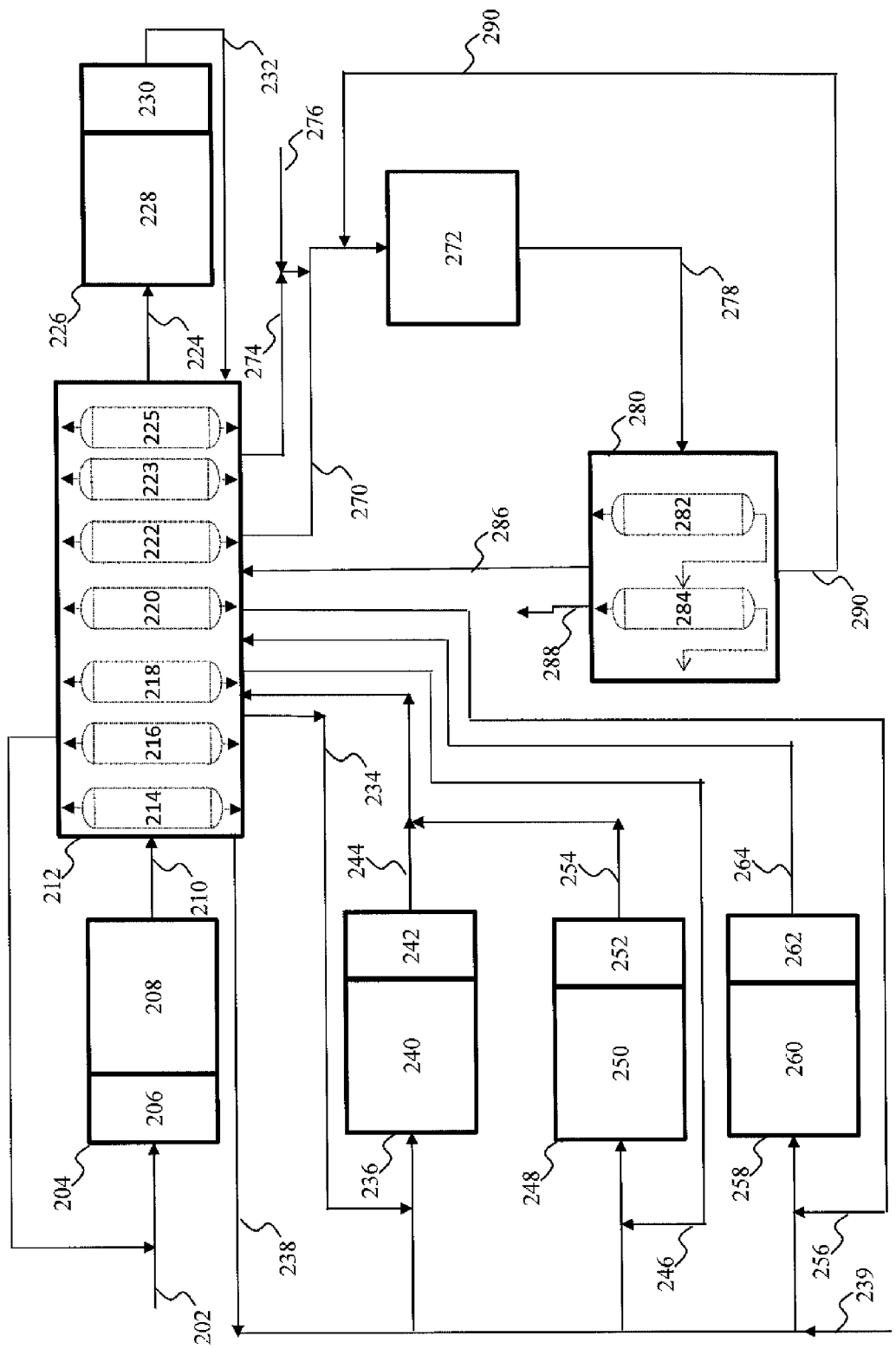
FIG. 6 is a simplified process flow diagram of a process for producing high purity 1-octenes according to embodiments disclosed herein.

FIG. 6 is a simplified process flow diagram of a system for producing 1-octenes according to embodiments herein. The overall concept for production of 1-octene is similar to that as described above with respect to 1-butene and 1-hexene. The 1-octene is converted to 2-nonene (beta olefin n+1). The hexenes, heptenes, and octenes react with propylene by metathesis to make a beta-olefin of one higher carbon length from the alpha-olefin, respectively. Reactors may be used to perform cross-metathesis between butenes and pentenes, respectively, to make higher carbon length olefins. A metathesis unit may then be used to convert the 2-nonene via metathesis with ethylene to produce 1-octene and propylene. In this manner, any linear olefin from carbon number 3 up to 8 can be added to the flow sheet and be completely utilized in the manufacture of 1-octene.

FIG. 6 is a simplified process flow diagram of a system for producing 1-octenes according to embodiments herein. A mixed n-butenes stream 202 is fed into an olefin conversion unit 204, which may include an upstream bed 206 of isomerization catalyst, such as MgO, and a downstream mixed catalyst bed 208 including a mixture of isomerization catalyst and metathesis catalyst, such as a 3:1 mixture of isomerization to metathesis catalyst. The n-butenes may be derived, for example, from the bottoms of a catalytic distillation unit (not shown) for separating linear butenes from isobutenes. The olefin conversion unit 204 converts 1-butene and 2-butene by isomerization and metathesis to ethylene, propylene, 2-pentene, and 3-hexene.

The reactor effluent 210 is then fed to the main separation train 212 for separation of the various products. The separation train 212 may include, for example, a deethylenizer 214, a depropylenizer 216, a debutanizer 218, a depentenizer 220, a dehexenizer 222, a deheptenizer 223, and a deoctenizer 225, among other possible configurations. For convenience, the flow streams are illustrated to/from the train 112, as opposed to the individual distillation towers.

The pentenes from the overhead 224 of the depentenizer are fed to a segregated olefin conversion unit 226. The segregated olefin conversion unit 226 may include an upstream bed 228 of isomerization catalyst and a downstream bed 230 of metathesis catalyst similar to that as described above. In the segregated OCU 226, 1-pentene and 2-pentene are isomerized in the isomerization reaction zone, producing an equilibrium mixture of 1-pentene and 2-pentene, which then react in the metathesis reaction zone to produce ethylene, propylene, butenes, 2-hexene, 3-hexene, 2-heptene, and 4-octene. The effluent 232 from the segregated OCU 226 are also fed to the main separation train 212.

The hexenes from the overhead 234 of the dehexenizer are fed to a segregated OCU 236 along with propylene 238 from the overhead of the depropylenizer and any fresh propylene 239, as needed. The segregated OCU 236 may include an upstream bed 240 of isomerization catalyst and a downstream bed 242 of metathesis catalyst as described above. In the isomerization reaction zone 240, an equilibrium mixture of 1-hexene, 2-hexene, and 3-hexene is produced. The 1-hexene then reacts with propylene in the metathesis reaction zone 242 to form ethylene and 2-heptene. The other hexenes react with propylene and ethylene to form butenes and pentenes. The effluent 244 from the segregated OCU 236 are also fed to the main separation train 212.

The heptenes from the overhead 246 of the deheptenizer are fed to a segregated OCU 248 along with propylene 238 from the overhead of the depropylenizer and any fresh propylene 239, as needed. The segregated OCU 248 may include an upstream bed 250 of isomerization catalyst and a downstream bed 252 of metathesis catalyst as described above. In the isomerization reaction zone 250, an equilibrium mixture of heptane isomers is produced. The 1-hexene then reacts with propylene in the metathesis reaction zone 252 to form ethylene and 2-octene. The other heptenes react with propylene and ethylene to form lighter olefins. The effluent 254 from the segregated OCU 248 are also fed to the main separation train 212.

The octenes from the overhead 256 of the deoctenizer are fed to a segregated OCU 258 along with propylene 238 from the overhead of the depropylenizer and any fresh propylene 239, as needed. The segregated OCU 258 may include an upstream bed 260 of isomerization catalyst and a downstream bed 262 of metathesis catalyst as described above. In the isomerization reaction zone 260, an equilibrium mixture of octane isomers is produced. The 1-octene then reacts with propylene in the metathesis reaction zone 262 to form ethylene and 2-nontene. The other octenes react with propylene and ethylene to form lighter olefins. The effluent 264 from the segregated OCU 258 are also fed to the main separation train 212.

The bottoms 270 from the deoctenizer, including 2-nonene, are fed to a metathesis reaction zone 272 along with ethylene 274 from the overhead of the deethylenizer and any fresh ethylene 276, as needed. 2-Nonene reacts with ethylene to form the 1-octene product and propylene. The reactor effluent 278 is then sent to a second separation train 280 including a deheptenizer 282 and a deoctenizer 284. The overhead 286 from the dehepteniser is fed back to the front of the main separation train 212. 1-Hexene product 288 is collected from the overhead of the dehexenizer. The bottoms 290 of the denonenizer contain unreacted nonenes, and may be recycled back to the metathesis reactor 272 for continued conversion.

The primary reactions taking place in the various reactors are as follows.
Olefin Conversion Unit 204
1-butene+2-butene↔propylene+2-pentene
1-butene+1-butene↔ethylene+3-hexene
Segregated OCU 226
2-pentene+2-pentene↔2-butene+3-hexene
1-pentene+2-pentene↔propylene+3-heptene
1-pentene+2-pentene↔1-butene+2-hexene
1-pentene+1-pentene↔ethylene+4-octene
Segregated OCU 236
1-hexene+propylene↔2-heptene+ethylene
2-hexene+propylene↔2-butene+1-pentene
3-hexene+propylene↔1-butene+2-pentene
Segregated OCU 248
1-heptene+propylene↔2-octene+ethylene
2-heptene+propylene↔2-butene+1-hexene
3-heptene+propylene↔1-butene+2-hexene
3-heptene+propylene↔1-pentene+2-entene
Segregated OCU 258
1-octene+propylene↔2-nonene+ethylene
2-octene+propylene↔2-butene+1-heptene
3-octene+propylene↔1-butene+2-heptene
4-octene+propylene↔2-pentene+1-hexene 4-octene+propylene↔1-pentene+2-hexene
Metathesis Reactor 272
2-nonene+ethylene↔1-octene+propylene Processes for the production of other alpha-olefins, such as 1-pentene and 1-heptene, are also contemplated according to embodiments herein. As described above for 1-hexene, two segregated OCU's were used to increase the carbon number of 1-pentene and 1-hexene; for 1-octene, four segregated OCU's were used. 1-Pentene production would require only a single segregated OCU, whereas 1-heptene production would require three segregated OCU's. The resulting 2-hexene and 2-octene containing streams would then be metathesized with ethylene to result in the desired 1-pentene and 1-heptene, respectively, recoverable at high purities.

In embodiments disclosed herein, the isomerization/metathesis reactors, and/or the metathesis-only reactors may be operated at a pressure between 2 and 40 atmospheres, and between 5 and 15 atmospheres in other embodiments. The reactors may be operated such that the reaction temperature is within the range from about 50° C. to about 600° C.; within the range from about 200° C. to about 450° C. in other embodiments; and from about 250° C. to about 400° C. in yet other embodiments. The isomerization and metathesis reactions may be performed at a weight hourly space velocity (WHSV) in the range from about 2 to about 200 in some embodiments, and from about 3 to about 40 in other embodiments.

The reactions may be carried out by contacting the olefin(s) with the isomerization and/or metathesis catalysts in the liquid phase or the gas phase, depending on structure and molecular weight of the olefin(s). If the reaction is carried out in the liquid phase, solvents or diluents for the reaction can be used. Aliphatic saturated hydrocarbons, e.g., pentanes, hexanes, cyclohexanes, dodecanes and aromatic hydrocarbons such as benzene and toluene are suitable. If the reaction is carried out in the gaseous phase, diluents such as saturated aliphatic hydrocarbons, for example, methane, ethane, and/or substantially inert gases, such as nitrogen and argon, may be present. For high product yield, the reactions may be conducted in the absence of significant amounts of deactivating materials such as water and oxygen.

The contact time needed to obtain a desirable yield of reaction products depends upon several factors such as the activity of the catalyst, temperature, pressure, and the structure of the olefin(s) to be isomerized and/or metathesized. Length of time during which the olefin(s) are contacted with catalyst can vary between 0.1 seconds and 4 hours, preferably from about 0.5 sec to about 0.5 hrs. The isomerization and metathesis reactions may be conducted batch-wise or continuously with fixed catalyst beds, slurried catalyst, fluidized beds, or by using any other conventional contacting techniques.

The catalyst contained within the metathesis reactor may be any known metathesis catalyst, including oxides of Group VIA and Group VIIA metals on supports. Catalyst supports can be of any type and could include alumina, silica, mixtures thereof, zirconia, and zeolites. In some embodiments, the metathesis catalyst is tungsten oxide on silica.

The double bond isomerization catalyst may be any known double bond isomerization catalyst. In some embodiments, the double bond isomerization catalyst may be magnesium oxide or calcium oxide, among other possible catalysts.

In some embodiments, the double bond isomerization catalyst may be an alumina-titania catalyst. The catalyst may be a γ-alumina-titania crystalline mixture including active sites that catalyze the positional isomerization of olefins, and may be in the form of pellets, extrudates, and the like, and will typically have an effective diameter of 0.5 mm to 5 mm, such as in the range from 1 mm to 4 mm, or in the range from 2 mm to 3 mm. In some embodiments, the alumina-titania catalyst may have a composition of titanium with a lower limit of 0.01, 1, 2, 3, 4, 5, 10, 15, 20, or 25 to an upper limit of 15, 20, 25, 30, 35, 40, 45, or 50 wt %, where any lower limit may be combined with any upper limit. γ-Alumina-titania catalyst herein may have a surface area in some embodiments greater than 200 $m^2/g$, in other embodiments greater than 250 $m^2/g$, in other embodiments greater than 300 $m^2/g$, in other embodiments greater than 350 $m^2/g$, and in other embodiments greater than 400 $m^2/g$. The γ-alumina-titania catalysts may be tolerant of oxygenated species that are typically considered a poison, such as to MgO type catalysts, may act as an oxygenate scavenger protecting downstream catalyst beds, and in some embodiments may have activity for dehydration of alcohols in addition to isomerization activity. The γ-alumina-titania catalysts may also be more forgiving with respect to cyclopentene purity of the feed, and may allow greater than 5 wt %, greater than 7.5 wt %, or even greater than 10 wt % cyclopentene to be present in the feed, potentially negating typical upstream processes required to remove cyclopentene from the feed. These γ-alumina-titania catalysts may be used alone, such as in an isomerization only reactor or in an isomerization catalyst bed in a segregated OCU, or may be used in admixture with other isomerization catalysts or metathesis catalysts.

While the disclosure includes a limited number of embodiments, those skilled in the art, having benefit of this disclosure, will appreciate that other embodiments may be devised which do not depart from the scope of the present disclosure. Accordingly, the scope should be limited only by the attached claims.

What is claimed:

1. A process for the production of olefins, the process comprising:
    (a) contacting propylene and a hydrocarbon mixture comprising a mixture of olefins having a carbon number n with a first metathesis catalyst to form a metathesis product comprising a beta-olefin having a carbon number n+1, an alpha-olefin having a carbon number n−1, as well as any unreacted propylene and olefins having a carbon number n;
    (b) fractionating the metathesis product to recover a fraction comprising the beta-olefin having a carbon number n+1;
    (c) contacting ethylene and the fraction comprising the beta-olefin having a carbon number n+1 with a second metathesis catalyst to form a second metathesis product comprising an alpha-olefin having a carbon number n and propylene; and
    (d) fractionating the second metathesis product to form a propylene fraction and a fraction comprising the alpha olefin having a carbon number n, wherein n is selected from the range of 4 to about 8.

2. The process of claim 1, wherein the hydrocarbon mixture comprises C4 olefins, and the alpha olefin having a carbon number n is 1-butene.

3. The process of claim 1, wherein the hydrocarbon mixture comprises C5 olefins, and the alpha olefin having a carbon number n is 1-pentene.

4. The process of claim 1, wherein the hydrocarbon mixture comprises C6 olefins, and the alpha olefin having a carbon number n is 1-hexene.

5. The process of claim 1, wherein the hydrocarbon mixture comprises C7 olefins, and the alpha olefin having a carbon number n is 1-heptene.

6. The process of claim 1, wherein the hydrocarbon mixture comprises C8 olefins, and the alpha olefin having a carbon number n is 1-octene.

7. A process for producing high purity 1-butene, the process comprising:
    contacting a hydrocarbon mixture comprising linear butenes with an isomerization catalyst to form an isomerization product comprising 2-butenes and 1-butenes;
    contacting propylene and the isomerization product with a first metathesis catalyst to form a first metathesis product comprising 2-pentene, propylene unreacted butenes, ethylene and 3-hexene;
    fractionating the first metathesis product to recover an ethylene fraction, a propylene fraction, a butene fraction, and a 2-pentene fraction;
    contacting the 2-pentene fraction and ethylene with a second metathesis catalyst, which may be the same or different than the first metathesis catalyst, to form a metathesis effluent comprising ethylene, propylene, 1-butene, and any unreacted 2-pentene; and
    fractionating the metathesis effluent to recover a 1-butene fraction, a C3− fraction, and a C5+ fraction.

8. The process of claim 7, further comprising feeding the C3− fraction and the first metathesis product to a common fractionation system.

9. The process of claim 7, further comprising recycling the C5+ fraction for continued conversion over the second metathesis catalyst.

10. The process of claim 7, further comprising recycling the butene fraction for continued conversion over the isomerization catalyst and the first metathesis catalyst.

11. A process for producing high purity 1-hexene, the process comprising:
    isomerizing and metathesizing a mixed C4 olefin stream comprising 1-butene and 2-butene to produce a first reaction product comprising ethylene, propylene, unreacted butenes, 2-pentene, and 3-hexene;
    isomerizing and metathesizing a mixed C5 olefin stream comprising 1-pentene and 2-pentene to produce a second reaction product comprising ethylene, propylene, n-butenes, unreacted pentenes, 3-hexene, 3-heptene, 2-hexene, and 4-octene;
    isomerizing and metathesizing propylene and a mixed C6 olefin stream comprising 1-hexene, 2-hexene, and 3-hexene to produce a third reaction product comprising ethylene, n-butenes, n-pentenes, and 2-heptene;
    fractionating the first, second, and third reaction products in a common fractionation system to recover an ethylene fraction, a propylene fraction, a butene fraction, a pentene fraction, a hexene fraction, and a heptene fraction comprising 2-heptene;
    metathesizing ethylene and the 2-heptene in the heptene fraction to form a metathesis product comprising propylene, 1-hexene, and any unreacted ethylene and 2-heptene; and
    fractionating the metathesis product to recover an C5− fraction, a 1-hexene product fraction, and a C7+ fraction.

12. The process of claim 11, further comprising feeding the C5− fraction to the common fractionation system.

13. The process of claim 11, further comprising recycling the butene fraction for continued conversion along with the mixed C4 olefin stream.

14. The process of claim 11, further comprising using at least a portion of the pentene fraction as the mixed C5 olefin stream.

15. The process of claim 11, further comprising using at least a portion of the hexene fraction as the mixed C6 olefin stream.

16. A process for producing high purity 1-octene, the process comprising:
    isomerizing and metathesizing a mixed C4 olefin stream comprising 1-butene and 2-butene to produce a first reaction product comprising ethylene, propylene, unreacted butenes, 2-pentene, and 3-hexene;
    isomerizing and metathesizing a mixed C5 olefin stream comprising 1-pentene and 2-pentene to produce a second reaction product comprising ethylene, propylene, n-butenes, unreacted pentenes, 3-hexene, 3-heptene, 2-hexene, and 4-octene;
    isomerizing and metathesizing propylene and a mixed C6 olefin stream comprising 1-hexene, 2-hexene, and 3-hexene to produce a third reaction product comprising ethylene, n-butenes, n-pentenes, and 2-heptene;
    isomerizing and metathesizing propylene and a mixed C7 olefin stream comprising 1-heptene, 2-heptene, and 3-heptene to produce a fourth reaction product comprising ethylene, n-butenes, n-pentenes, n-hexenes, and 2-octene;
    isomerizing and metathesizing propylene and a mixed C8 olefin stream comprising 1-octene, 2-octene, 3-octene, and 4-octene to produce a fifth reaction product comprising ethylene, n-butenes, n-pentenes, n-hexenes, and 2-nonene;
    fractionating the first, second, third, fourth, and fifth reaction products in a common fractionation system to recover an ethylene fraction, a propylene fraction, a butene fraction, a pentene fraction, a hexene fraction, a heptene fraction, an octene fraction, and a nonene fraction comprising 2-nonene;
    metathesizing ethylene and the 2-nonene in the nonene fraction to form a metathesis product comprising propylene, 1-octene, and any unreacted ethylene and 2-nonene; and
    fractionating the metathesis product to recover an C7− fraction, a 1-octene product fraction, and a C9+ fraction.

17. The process of claim 16, further comprising feeding the C7− fraction to the common fractionation system.

18. The process of claim 16, further comprising recycling the butene fraction for continued conversion along with the mixed C4 olefin stream.

19. The process of claim 16, further comprising using at least a portion of the pentene fraction as the mixed C5 olefin stream.

20. The process of claim 16, further comprising using at least a portion of the hexene fraction as the mixed C6 olefin stream.

21. The process of claim 16, further comprising using at least a portion of the heptene fraction as the mixed C7 olefin stream.

22. The process of claim 16, further comprising using at least a portion of the octene fraction as the mixed C8 olefin stream.

* * * * *